United States Patent [19]

McCredy

[11] Patent Number: 5,741,269

[45] Date of Patent: Apr. 21, 1998

[54] MEDICAL VACUUM DEVICE

[76] Inventor: Doug McCredy, 28 Monroe St., Matawan, N.J. 07747

[21] Appl. No.: 752,172

[22] Filed: Nov. 18, 1996

[51] Int. Cl.$^6$ ........................................... A61B 17/00
[52] U.S. Cl. ............................... 606/106; 604/313
[58] Field of Search ........................... 606/760, 763, 606/765, 768, 769; 604/27, 35, 36, 37, 54, 93, 212, 313, 319; 15/320, 322, 353

[56] References Cited

U.S. PATENT DOCUMENTS 5,009,635  4/1991  Scarberry ........................... 604/37

FOREIGN PATENT DOCUMENTS 1136018  11/1982  Canada.

*Primary Examiner*—Michael Buiz
*Assistant Examiner*—William W. Lewis

[57] ABSTRACT

A medical vacuum device including a vacuum. A hose is received within the vacuum and into communication with a suction pump of the vacuum. The device includes a suction tube having a conical configuration. The suction tube couples with the hose. The tube can be extended into the throat of a choking victim in order to suck out the item of food lodged in the victims throat.

2 Claims, 3 Drawing Sheets

MEDICAL VACUUM DEVICE

BACKGROUND OF THE INVENTION

1. Field of the Invention

The present invention relates to a medical vacuum device and more particularly pertains to dislodging food stuck in a choking victims throat with a medical vacuum device.

2. Description of the Prior Art

The use of aspiration-type devices is known in the prior art. More specifically, aspiration-type devices heretofore devised and utilized for the purpose of removing objects from cavities are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,902,276 to Zakko discloses an apparatus and method for removing obstructions in bodily organs or cavities.

U.S. Pat. No. 4,861,333 to Meador discloses an animal aspirating and irrigating apparatus.

U.S. Pat. No. Des. 321,937 to Young discloses the ornamental design for a food dislodging aid for choking victims.

U.S. Pat. No. 5,429,601 to Conley et al. discloses an aspiration control system.

U.S. Pat. No. 5,195,961 to Takahashi et al. discloses an aspirator.

U.S. Pat. No. Des. 287,893 to Fujii et al. discloses the ornamental design for a portable vacuum cleaner.

While these devices fulfill their respective, particular objective and requirements, the aforementioned patents do not describe a medical vacuum device for dislodging food stuck in a choking victims throat.

In this respect, the medical vacuum device according to the present invention substantially departs from the conventional concepts and designs of the prior art, and in doing so provides an apparatus primarily developed for the purpose of dislodging food stuck in a choking victims throat.

Therefore, it can be appreciated that there exists a continuing need for new and improved medical vacuum device which can be used for dislodging food stuck in a choking victims throat. In this regard, the present invention substantially fulfills this need.

SUMMARY OF THE INVENTION

In the view of the foregoing disadvantages inherent in the known types of aspiration-type devices now present in the prior art, the present invention provides an improved medical vacuum device. As such, the general purpose of the present invention, which will be described subsequently in greater detail, is to provide a new and improved medical vacuum device and method which has all the advantages of the prior art and none of the disadvantages.

To attain this, the present invention essentially comprises a housing having a rectangular configuration. The housing has an open front, a closed rear, a top, a bottom, and opposed sides. The housing has a suction pump disposed therein inwardly of the open front. The housing has a rechargeable battery disposed therein in cooperation with the suction pump. A recharging plug extends outwardly of the closed rear of the housing for coupling with an electrical outlet. The top has a handle secured thereto. The bottom has four short legs disposed in four corners thereof. The open front has a lid removably secured thereover. The lid has a central aperture therethrough leading into communication with the suction pump. The device includes a hose having an open first end and an open second end. The open first end is received within the central aperture in the lid and into communication with the suction pump. The open second end is internally threaded. The device includes a flexible and transparent suction tube having a conical configuration. The flexible and transparent suction tube has an open wide end and an open tapered end. The open wide end has a threaded flange extending outwardly therefrom. The threaded flange couples with the internally threaded open second end of the hose.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved medical vacuum device which has all the advantages of the prior art aspiration-type devices and none of the disadvantages.

It is another object of the present invention to provide a new and improved medical vacuum device which may be easily and efficiently manufactured and marketed.

It is a further object of the present invention to provide a new and improved medical vacuum device which is of durable and reliable construction.

An even further object of the present invention is to provide a new and improved medical vacuum device which is susceptible of a low cost of manufacture with regard to both materials and labor, and which accordingly is then susceptible of low prices of sale to the consuming public, thereby making such a medical vacuum device economically available to the buying public.

Even still another object of the present invention is to provide a new and improved medical vacuum device for dislodging food stuck in a choking victims throat.

Lastly, it is an object of the present invention to provide a new and improved medical vacuum device including a vacuum. A hose is received within the vacuum and into communication with a suction pump of the vacuum. The device includes a suction tube having a conical configuration. The suction tube couples with the hose. The tube can be extended into the throat of a choking victim in order to suck out the item of food lodged in the victims throat.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
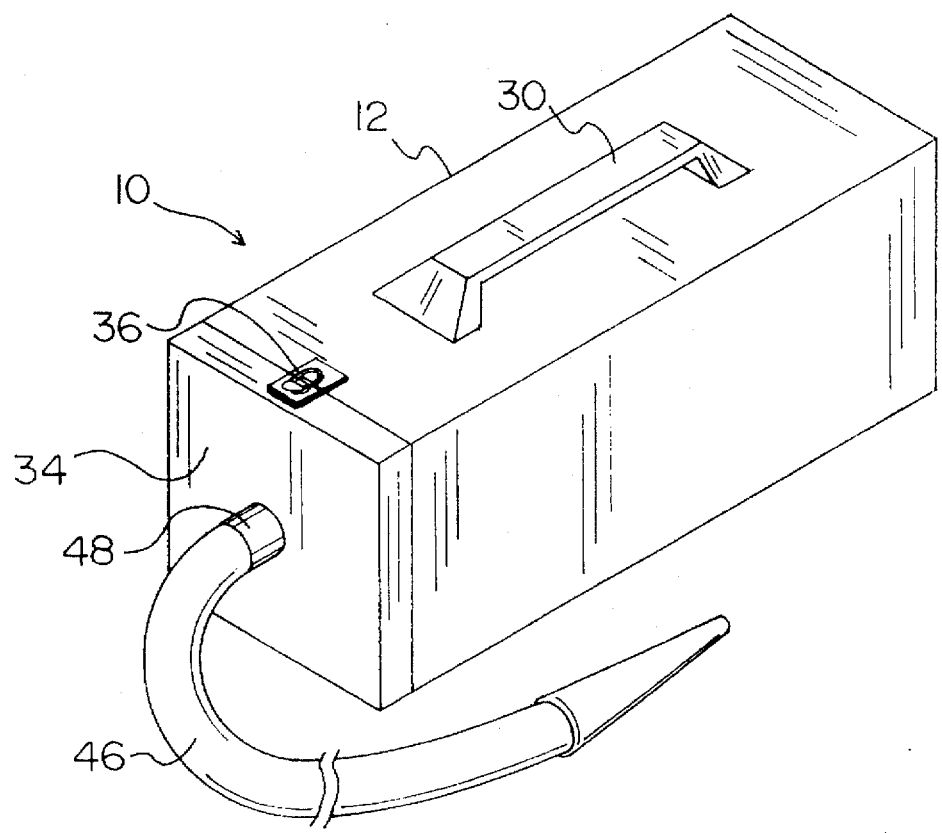
FIG. 1 is a perspective view of the preferred embodiment of the medical vacuum device constructed in accordance with the principles of the present invention.
Figure 2:
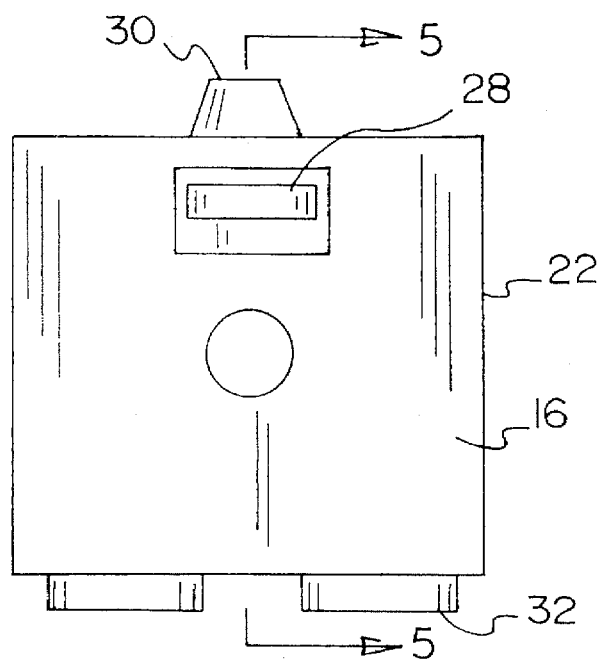
FIG. 2 is a rear elevation view of the present invention.
Figure 3:
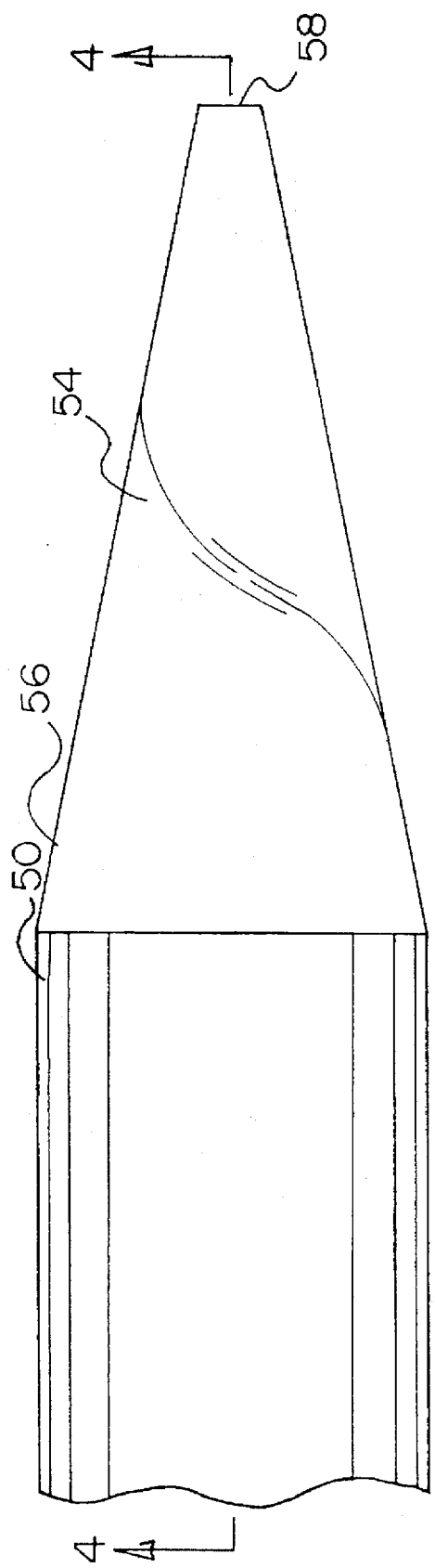
FIG. 3 is a fragmentary side view of the hose and flexible suction tube of the present invention.
Figure 4:
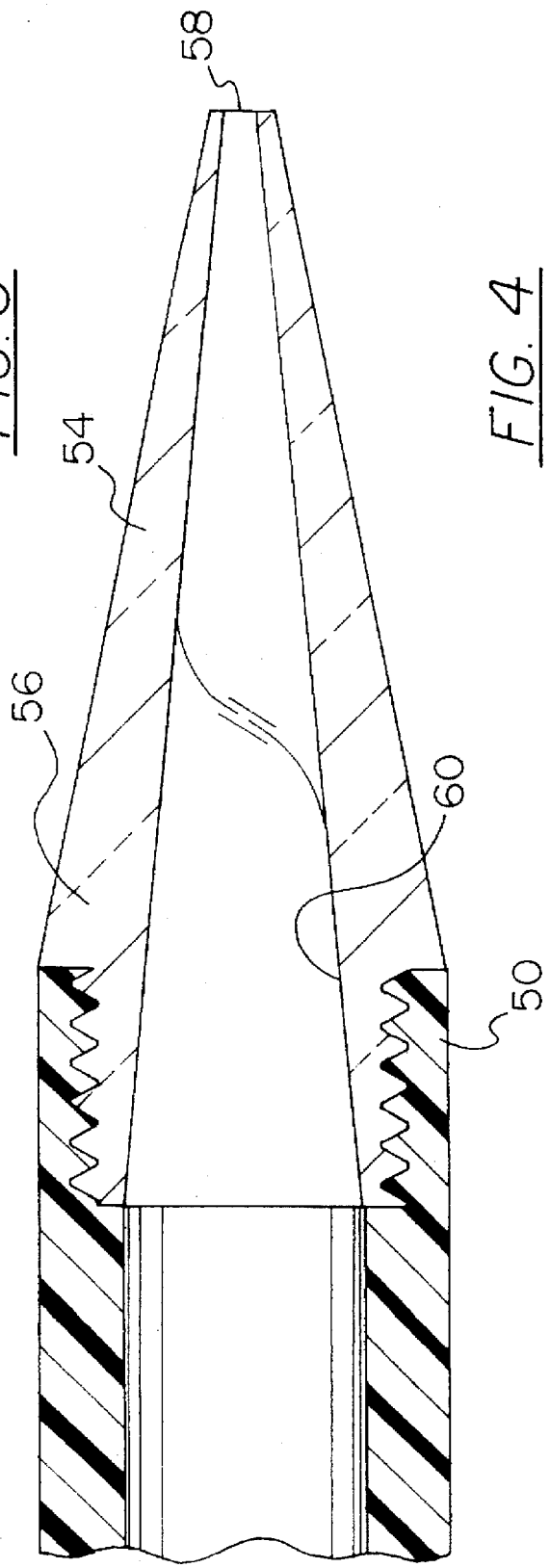
FIG. 4 is a cross-sectional view as taken along line 4—4 of FIG. 3.
Figure 5:
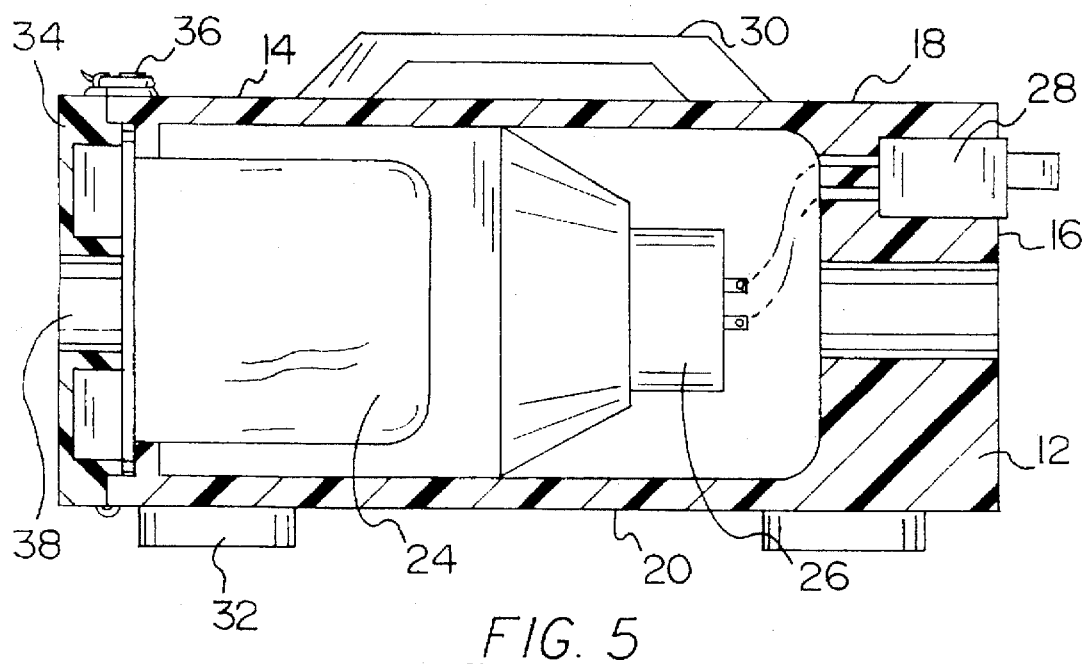
FIG. 5 is a cross-sectional view as taken along line 5—5 of FIG. 2.

With reference now to the drawings, and in particular, to FIGS. 1 through thereof, the preferred embodiment of the new and improved medical vacuum device embodying the principles and concepts of the present invention and generally designated by the reference number 10 will be described.

Specifically, it will be noted in the various Figures that the device relates to a medical vacuum device for dislodging food stuck in a choking victims throat. In its broadest context, the device consists of a housing, a hose and a flexible and transparent suction tube. Such components are individually configured and correlated with respect to each other so as to attain the desired objective.

The device 10 includes a housing 12 having a rectangular configuration. The housing 12 has an open front 14, a closed rear 16, a top 18, a bottom 20, and opposed sides 22. The housing 12 has a suction pump 24 disposed therein inwardly of the open front 14. The housing 12 has a rechargeable battery 26 disposed therein in cooperation with the suction pump 24. The use of the rechargeable battery 26 allows for the portability of the device 10. A recharging plug 28 extends outwardly of the closed rear 16 of the housing 12 for coupling with an electrical outlet. The top 18 has a handle 30 secured thereto. The bottom 20 has four short legs 32 disposed in four corners thereof. The open front 14 has a lid 34 removably secured thereover. A clip arrangement 36 facilitates the securement of the lid 34 to the open front 14. The lid 34 has a central aperture 38 therethrough leading into communication with the suction pump 24.

Next, the device 10 includes a hose 46 having an open first end 48 and an open second end 50. The open first end 48 is received within the central aperture 38 in the lid 34 and into communication with the suction pump 24. The open second end 50 is internally threaded. The open first end 48 of the hose 46 simply slides in and out of the central aperture 38.

Figure 6:
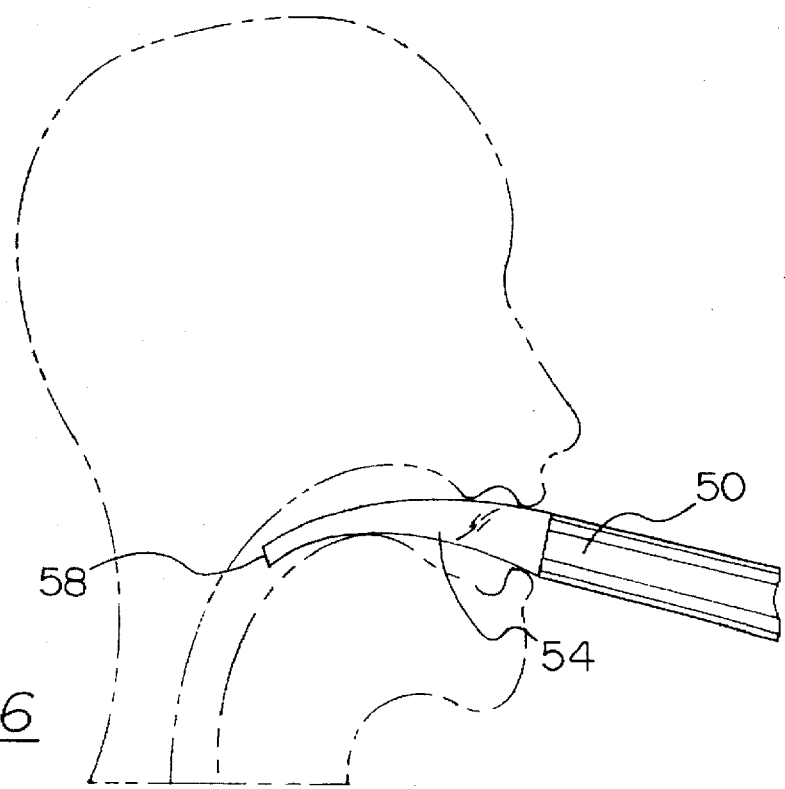
FIG. 6 is a side view of the present invention displayed in use.

Lastly, the device 10 includes a flexible and transparent suction tube 54 having a conical configuration. The flexible and transparent suction tube 54 has an open wide end 56 and an open tapered end 58. The open wide end 56 has a threaded flange 60 extending outwardly therefrom. The threaded flange 60 couples with the internally threaded open second end 50 of the hose 46. The device 10 in use is illustrated in FIG. 6 where the flexible and transparent suction tube 54 in inserted into the choking victims throat. The sucking action will dislodge the food from the victim's throat to restore free breathing. The suction tube 54 can then be removed and discarded. A replacement suction tube 54 is then reattached to the hose 46 for the next use.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A medical vacuum device for dislodging food stuck in a choking victims throat comprising, in combination:

a housing having a rectangular configuration, the housing having an open front, a closed rear, a top, a bottom, and opposed sides, the housing having a suction pump disposed therein inwardly of the open front, the housing having a rechargeable battery disposed therein in cooperation with the suction pump, a recharging plug extending outwardly of the closed rear of the housing for coupling with an electrical outlet, the top having a handle secured thereto, the bottom having four short legs disposed in four corners thereof, the open front having a lid removably secured thereover, the lid having a central aperture therethrough leading into communication with the suction pump;

a hose having an open first end and an open second end, the open first end received within the central aperture in the lid and into communication with the suction pump, the open second end being internally threaded; and a flexible and transparent suction tube having a conical configuration, the flexible and transparent suction tube having an open wide end and an open tapered end, the open wide end having a threaded flange extending outwardly therefrom, the threaded flange coupling with the internally threaded open second end of the hose.

2. The medical vacuum device as set forth in claim 1 wherein the flexible and transparent suction tube is disposable.

* * * * *